(12) United States Patent
Lee et al.

(10) Patent No.: US 9,579,071 B2
(45) Date of Patent: Feb. 28, 2017

(54) X-RAY IMAGING APPARATUS AND CONTROL METHOD THEREOF

(71) Applicant: SAMSUNG ELECTRONICS CO., LTD., Suwon-si (KR)

(72) Inventors: Jae Hak Lee, Yongin-si (KR); Dong Goo Kang, Hwaseong-si (KR); Sung Hoon Kang, Suwon-si (KR); Young Hun Sung, Hwaseong-si (KR); Seok Min Han, Seongnam-si (KR)

(73) Assignee: SAMSUNG ELECTRONICS CO., LTD., Suwon-si (KR)

( * ) Notice: Subject to any disclaimer, the term of this patent is extended or adjusted under 35 U.S.C. 154(b) by 111 days.

(21) Appl. No.: 14/338,805

(22) Filed: Jul. 23, 2014

(65) Prior Publication Data
US 2015/0063537 A1   Mar. 5, 2015

(30) Foreign Application Priority Data

Aug. 29, 2013 (KR) .................. 10-2013-0103241

(51) Int. Cl.
*A61B 6/00*   (2006.01)
*A61B 6/03*   (2006.01)
*A61B 6/02*   (2006.01)

(52) U.S. Cl.
CPC ............ *A61B 6/022* (2013.01); *A61B 6/4007* (2013.01); *A61B 6/032* (2013.01); *A61B 6/4441* (2013.01)

(58) Field of Classification Search
CPC ....... A61B 6/022; A61B 6/032; A61B 6/4007; A61B 6/4441

USPC ....................... 378/9, 41, 196, 197
See application file for complete search history.

(56) References Cited

U.S. PATENT DOCUMENTS

| | | | | |
|---|---|---|---|---|
| 5,583,345 A * | 12/1996 | Kohgami | ............... | A61B 6/025 250/336.1 |
| 6,256,372 B1 * | 7/2001 | Aufrichtig | ............. | A61B 6/022 348/E13.005 |
| 6,307,914 B1 * | 10/2001 | Kunieda | .................. | A61B 6/12 378/65 |
| 6,449,333 B1 * | 9/2002 | Yamasaki | ............. | A61B 6/022 378/41 |
| 6,720,966 B2 * | 4/2004 | Barth | .................... | G06T 11/005 250/363.04 |

(Continued)

FOREIGN PATENT DOCUMENTS

| | | |
|---|---|---|
| JP | 2009-022788 A | 2/2009 |
| JP | 2010-526558 A | 8/2010 |

*Primary Examiner* — Allen C. Ho
(74) *Attorney, Agent, or Firm* — Sughrue Mion, PLLC

(57) ABSTRACT

Disclosed herein is an X-ray imaging apparatus including: an X-ray generator including a first X-ray source configured to irradiate a first X-ray onto an object, and at least one second X-ray source spaced apart from the first X-ray source and configured to irradiate at least one second X-ray onto the object; an X-ray detector configured to detect the first X-ray which has propagated through the object and the at least one second X-ray which has propagated through the object; and an image processor configured to produce a first X-ray image of the object based on the detected first X-ray, to produce at least one second X-ray image of the object based on the detected at least one second X-ray, and to produce a stereoscopic image of the object based on the first X-ray image and the at least one second X-ray image.

17 Claims, 13 Drawing Sheets

(56) References Cited

U.S. PATENT DOCUMENTS

| | | | |
|---|---|---|---|
| 6,763,083 B2* | 7/2004 | Fernandez | G01V 5/0058 378/196 |
| 6,778,850 B1* | 8/2004 | Adler | A61B 6/12 378/4 |
| 6,914,959 B2* | 7/2005 | Bailey | A61B 6/022 378/41 |
| 6,922,457 B2* | 7/2005 | Nagata | A61B 6/032 378/15 |
| 7,035,371 B2* | 4/2006 | Boese | G21K 4/00 378/41 |
| 7,204,640 B2* | 4/2007 | Fu | A61N 5/1049 378/205 |
| 7,209,538 B2* | 4/2007 | Sukovic | A61B 6/022 378/189 |
| 7,227,925 B1* | 6/2007 | Mansfield | A61N 5/1049 378/41 |
| 7,239,684 B2* | 7/2007 | Hara | A61N 5/1049 378/65 |
| 7,302,033 B2* | 11/2007 | Carrano | A61B 6/022 378/41 |
| 7,336,758 B2* | 2/2008 | Seto | A61B 6/12 378/162 |
| 7,558,368 B2* | 7/2009 | Klingenbeck-Regn | A61B 6/022 378/41 |
| 7,620,144 B2* | 11/2009 | Bodduluri | A61B 6/02 378/41 |
| 7,684,647 B2* | 3/2010 | Fu | G06K 9/32 345/630 |
| 7,693,256 B2* | 4/2010 | Brahme | A61B 6/022 378/41 |
| 7,715,520 B2* | 5/2010 | Nagata | A61B 6/032 378/16 |
| 7,806,589 B2* | 10/2010 | Tashman | A61B 5/1038 378/193 |
| 7,809,102 B2* | 10/2010 | Brada | A61B 6/022 378/41 |
| 7,826,585 B2* | 11/2010 | Proksa | A61B 6/032 378/5 |
| 7,835,500 B2* | 11/2010 | Fu | G06T 7/0026 128/922 |
| 7,933,378 B2* | 4/2011 | Proksa | A61B 6/032 378/9 |
| 7,949,089 B2* | 5/2011 | Dafni | A61B 6/032 378/9 |
| 7,978,813 B2* | 7/2011 | Yoshimura | A61B 6/14 378/38 |
| 8,094,778 B2* | 1/2012 | Sendai | A61B 6/022 378/114 |
| 8,180,017 B2* | 5/2012 | Forthmann | A61B 6/032 378/156 |
| 8,465,204 B2* | 6/2013 | Kamiya | A61B 10/0275 378/204 |
| 8,559,596 B2* | 10/2013 | Thomson | G06T 7/0014 378/20 |
| 8,705,817 B2* | 4/2014 | Saint Felix | A61B 5/4504 382/128 |
| 8,817,948 B2* | 8/2014 | Kusunoki | H04N 13/0221 378/37 |
| 8,908,826 B2* | 12/2014 | Bernhardt | A61B 6/022 378/42 |
| 8,917,813 B2* | 12/2014 | Maurer, Jr. | A61N 5/10 378/197 |
| 9,025,840 B2* | 5/2015 | Waechter-Stehle | G06T 7/2053 378/98.12 |
| 9,036,777 B2* | 5/2015 | Ohishi | A61B 6/022 378/41 |
| 9,049,996 B2* | 6/2015 | Tsujii | A61B 6/022 |
| 9,149,239 B2* | 10/2015 | Lee | A61B 6/022 |
| 9,277,893 B2* | 3/2016 | Tsukagoshi | A61B 6/022 |
| 9,427,201 B2* | 8/2016 | West | A61B 6/466 |
| 2006/0227936 A1 | 10/2006 | Dong et al. | |
| 2010/0040196 A1* | 2/2010 | Zhang | A61B 6/022 378/42 |
| 2010/0067662 A1 | 3/2010 | Pietig et al. | |
| 2012/0321156 A1 | 12/2012 | Waechter-Stehle et al. | |

\* cited by examiner

FIG. 8

| ANGIOGRAPHY MODE | PROTOCOL 1 | | PROTOCOL 2 | | PROTOCOL 3 | |
|---|---|---|---|---|---|---|
| | FIRST SOURCE | SECOND SOURCE | FIRST SOURCE | SECOND SOURCE | FIRST SOURCE | SECOND SOURCE |
| Fluoroscopy | ON | OFF | ON | ON | ON | OFF |
| DSA | ON | OFF | ON | ON | ON | ON |
| Roadmapping | ON | OFF | ON | ON | ON | ON |

(a)  (b)

X-RAY IMAGING APPARATUS AND CONTROL METHOD THEREOF

CROSS-REFERENCE TO RELATED APPLICATION

This application claims priority from Korean Patent Application No. 10-2013-0103241, filed on Aug. 29, 2013 in the Korean Intellectual Property Office, the disclosure of which is incorporated herein by reference in its entirety.

BACKGROUND

1. Field

Exemplary embodiments relate to an X-ray imaging apparatus which is configured for irradiating X-rays onto an object to produce an X-ray image, and a control method thereof.

2. Description of the Related Art

An X-ray imaging apparatus is used to check, diagnose, or detect the internal materials, tissue, or structure of an object, such as a human body, an animal, or a baggage case, using X-rays (also called Roentgen rays). Specifically, the X-ray imaging apparatus is used to detect an abnormal tissue or material, such as a human body's inside lesions, in order to understand the inside structure of an object or a component, or to scan baggage at an airport.

The X-ray imaging apparatus visualizes the inside of an object, such as a human body, by placing the object on a stand or at a predetermined location, irradiating X-rays onto the object in a specific direction, for example, in a vertical direction or in a horizontal direction, then detecting the X-rays which propagate through the object, and producing an X-ray image based on the detected X-rays.

The X-ray imaging apparatus visualizes the inside structure of an object based on a phenomenon that X-rays show different transmission or absorption characteristics based on the properties (for example, densities) of materials constituting an object.

The X-ray imaging apparatus includes Computed Tomography (CT), Full Field Digital Mammography (FFDM), and an X-ray imaging apparatus for angiography, which produce X-ray images by using different kinds of X-rays.

When the X-ray imaging apparatus for angiography is used, an intervention specialist makes an incision of about 3 mm in a target area of a patient's skin, inserts a thin tube of about 2 mm called a catheter into the patient's blood vessel, and injects a medication such as a contrast medium so that the patient's blood vessels (veins and arteries) are shown through an X-ray image. An X-ray imaging apparatus for angiography, which is generally used for angiography at hospitals, provides two-dimensional (2D) X-ray images in real time using a single X-ray source and an X-ray detector. Accordingly, when a specialist performs a procedure with operation tools (e.g., catheter) while seeing complicated blood vessel images, the specialist may have difficulty in distinguishing the front and rear locations of the blood vessels and the front and rear locations of the tools and the blood vessels.

SUMMARY

Therefore, it is an aspect of one or more exemplary embodiments to provide an X-ray imaging apparatus for improving accuracies of diagnosis and procedures using X-ray images by producing a stereoscopic image of the inside of an object using a plurality of X-ray sources, and providing (displaying) the stereoscopic image to a user, and a control method which is executable by using the X-ray imaging apparatus.

It is another aspect of one or more exemplary embodiments to provide an X-ray imaging apparatus for selectively using a plurality of X-ray sources according to a radiography mode, and a control method which is executable by using the X-ray imaging apparatus.

It is another aspect of one or more exemplary embodiments to provide an X-ray imaging apparatus for adjusting a cubic effect (depth) of a stereoscopic image that is to be produced by adjusting a distance between a plurality of X-ray sources, and changing a viewpoint or a viewing angle by rotating an X-ray generator and an X-ray detector that face each other, and a control method which is executable by using the X-ray imaging apparatus.

Additional aspects of the exemplary embodiments will be set forth in part in the description which follows and, in part, will be obvious from the description, or may be learned by practice of the exemplary embodiments.

In accordance with one aspect of one or more exemplary embodiments, an X-ray imaging apparatus includes: an X-ray generator including a first X-ray source configured to irradiate a first X-ray onto an object, and at least one second X-ray source which is spaced apart from the first X-ray source and configured to irradiate at least one second X-ray onto the object; an X-ray detector configured to detect the first X-ray which has propagated through the object and the at least one second X-ray which has propagated through the object; and an image processor configured to produce a first X-ray image of the object based on the detected first X-ray, to produce at least one second X-ray image of the object based on the detected at least one second X-ray, and to produce a stereoscopic image of the object based on the first X-ray image and the at least one second X-ray image.

Each of the first X-ray source and the second X-ray source may be spaced by a predetermined distance apart from a central axis of a casing which constitutes an external appearance of the X-ray generator.

One of the first X-ray source and the second X-ray source may be disposed on a central axis of a casing which constitutes an external appearance of the X-ray generator, and the other one of the first X-ray source and the second X-ray source may be disposed at an edge of the casing.

The X-ray imaging apparatus may further include: an input device configured to receive, from a user, at least one from among a radiography mode selection command, a translation command for translating the first X-ray source and/or the second X-ray source, and a rotation command for rotating the X-ray generator and the X-ray detector; and a controller configured to control the X-ray generator and the X-ray detector based on the at least one command which is received via the input device.

The controller may be further configured to drive at least one of the first X-ray source and the at least one second X-ray source based on the radiography mode selection command which is received via the input device.

The controller may be further configured to adjust a baseline distance between the first X-ray source and the at least one second X-ray source based on the translation command which is received via the input device.

The controller may be further configured adjust the baseline distance to within a range of between 5 centimeters and 10 centimeters.

The controller may be further configured to rotate the X-ray generator and the X-ray detector based on the rotation command which is received via the input device.

A dosage of the at least one second X-ray may be less than a dosage of the first X-ray.

The image processor may be configured to cause a picture quality of the first X-ray image to be substantially identical to a picture quality of the at least one second X-ray image.

The X-ray imaging apparatus may further include a display device configured to display the stereoscopic image of the object.

In accordance with another aspect of one or more exemplary embodiments, a control method which is executable by using an X-ray imaging apparatus includes: irradiating a first X-ray onto an object; detecting the first X-ray which has propagated through the object and using the detected first X-ray to produce a first X-ray image of the object; irradiating at least one second X-ray onto the object at a location spaced by a predetermined distance apart from a location at which the first X-ray has been irradiated; detecting the at least one second X-ray which has propagated through the object and using the detected at least one second X-ray to produce at least one second X-ray image of the object; and producing a stereoscopic image of the object based on the first X-ray image and the at least one second X-ray image.

A dosage of the at least one second X-ray may be less than a dosage of the first X-ray.

Before producing the stereoscopic image of the object, the control method may further include causing a picture quality of the first X-ray image to be substantially identical to a picture quality of the at least one second X-ray image.

The control method may further include displaying each of the first X-ray image and the at least one second X-ray image on different respective screens.

The control method may further include displaying the stereoscopic image of the object.

Therefore, according to the X-ray imaging apparatus and the control method thereof, it is possible to improve accuracies of diagnosis and procedures using X-ray images by producing a stereoscopic image of the inside of an object by using a plurality of X-ray sources, and providing (displaying) the stereoscopic image to a user.

Further, according to the X-ray imaging apparatus and the control method thereof, it is possible to selectively use a plurality of X-ray sources based on a radiography mode.

In addition, it is possible to adjust a cubic effect (depth) of a stereoscopic image that is to be produced by adjusting a distance between a plurality of X-ray sources, and to change a viewpoint or a viewing angle by rotating an X-ray generator and an X-ray detector that face each other.

BRIEF DESCRIPTION OF THE DRAWINGS

These and/or other aspects will become apparent and more readily appreciated from the following description of exemplary embodiments, taken in conjunction with the accompanying drawings of which:

FIG. 8 is a table showing examples of radiography protocols according to angiography modes, which are used upon radiography (angiography) using two X-ray sources;

DETAILED DESCRIPTION

Figure 1:
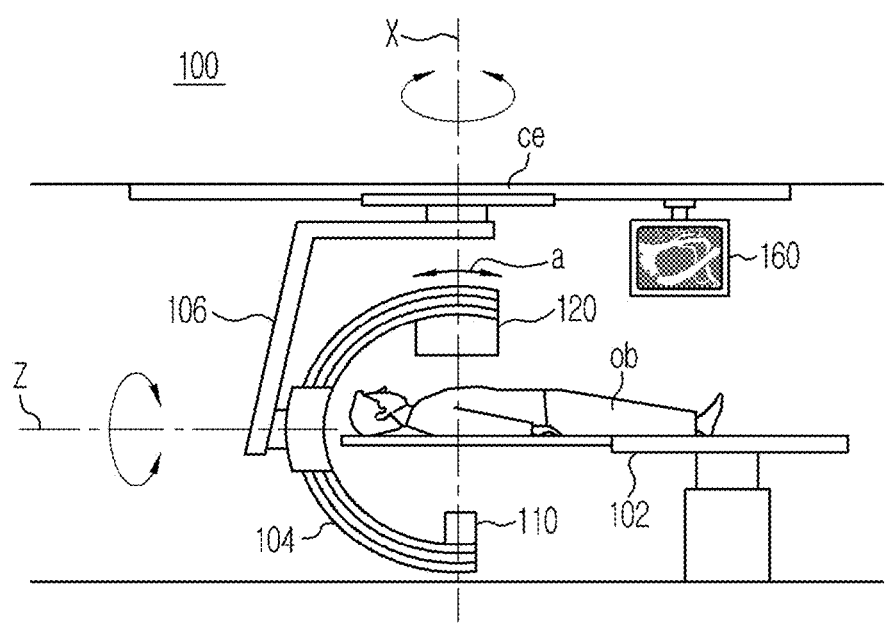
FIG. 1 illustrates an external appearance of an X-ray imaging apparatus according to an exemplary embodiment.

Reference will now be made in detail to exemplary embodiments, examples of which are illustrated in the accompanying drawings, wherein like reference numerals refer to like elements throughout.

For easy understanding and convenience of description in describing the exemplary embodiments with reference to FIGS. 1 to 10, an example in which one or more exemplary embodiments are applied to an X-ray imaging apparatus for angiography will be described. However, the exemplary embodiments are not limited to the X-ray imaging apparatus for angiography, and may be applied to other kinds of X-ray imaging apparatuses. In other words, although the exemplary embodiments are described based on an X-ray imaging apparatus for angiography, the scope of the exemplary embodiments would be not limited to an X-ray imaging apparatus for angiography.

FIG. 1 illustrates an external appearance of an X-ray imaging apparatus according to an exemplary embodiment.

As illustrated in FIG. 1, an X-ray imaging apparatus 100 may include a table 102 on which an object (e.g., a patient) ob that is to be examined or diagnosed is laid.

The X-ray imaging apparatus 100 may include an X-ray generator 110 configured to generate an X-ray and irradiate the X-ray onto the object ob, and an X-ray detector 120 disposed to face the X-ray generator 110 and configured to detect the X-ray which has propagated through the object ob. While an X-ray is irradiated, the object ob, that is, the patient, may be placed between the X-ray generator 110 and the X-ray detector 120. The X-ray detector 120 may transmit detected information to a controller or a processor via wired/wireless communication.

As illustrated in FIG. 1, the X-ray generator 110 and the X-ray detector 120 may be respectively disposed at both ends of a C-arm 104, wherein both ends of the C-arm 104 face each other. The C-arm 104 may be rotatable with respect to a horizontal axis represented as Z-axis. The C-arm 104 may rotate in a circular or semicircular motion as indicated by an arrow a. The C-arm 104 may be attached on a support 106 connected to a ceiling ce, and the support 106 may be rotatable with respect to a vertical axis represented as X-axis. Through rotations of the C-arm 104 and the support 106, X-ray images of various regions of interest (ROI) of the patient ob may be acquired in different directions. X-ray images of the patient ob, which are acquired by performing predetermined image processing on information detected by the X-ray detector 120, are displayed on a display unit (also referred to herein as a "display device" and/or as a "display") 160 which is connected to the ceiling ce.

Figure 2:
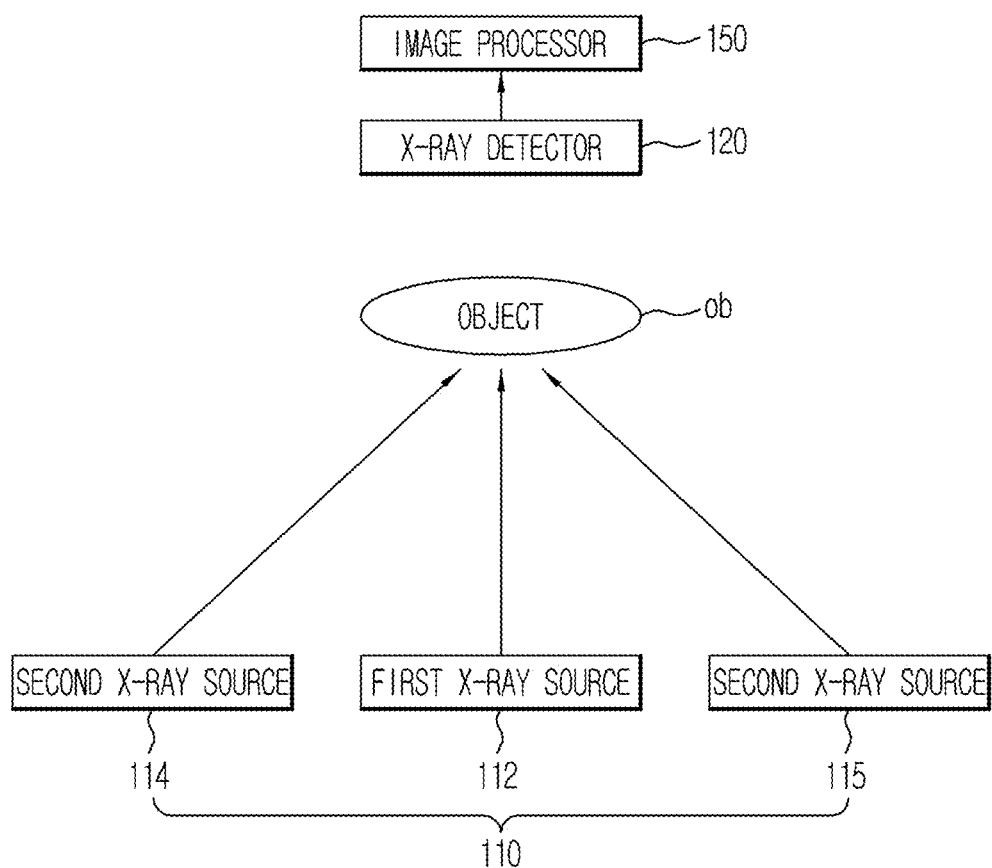
FIG. 2 is a view for describing a concept of X-ray detection and X-ray image production using an X-ray imaging apparatus.

FIG. 2 is a view for describing a concept of X-ray detection and X-ray image production using an X-ray imaging apparatus.

As illustrated in FIG. 2, an X-ray imaging apparatus 100 may include an X-ray generator 110 configured to generate X-rays and to irradiate the X-rays onto an object ob, an X-ray detector 120 configured to detect the X-rays which have propagated through the object ob and to convert the X-rays into electrical signals, and an image processor 150 configured to read an X-ray image from the electrical signals converted by the X-ray detector 120, and to perform predetermined image processing on the X-ray image.

As illustrated in FIG. 2, the X-ray generator 110 may include a first X-ray source 112 and one or more second X-ray sources 114 and 115, wherein each of the X-ray sources 112, 114, and 115 irradiates an X-ray onto the object ob under the control of a user or a controller. Accordingly, the X-ray generator 110 may irradiate X-rays sequentially or simultaneously several times toward the object ob and the X-ray detector 120.

The X-ray detector 120 may detect the X-rays which are irradiated by the first and second X-ray sources 112, 114, and 115 and which then have propagated through the object ob, convert the X-rays into electrical signals, and store the electrical signals. The image processor 150 may produce a plurality of X-ray images which respectively correspond to the X-rays irradiated by the X-ray sources 112, 114, and 115, based on the electrical signals.

Accordingly, the X-ray imaging apparatus 100 may acquire a plurality of X-ray images of the object ob, taken at different angles, via the plurality of X-ray sources 112, 114, and 115, and if the angles are within a predetermined angle range, the X-ray imaging apparatus 100 may combine the plurality of X-ray images to produce a stereoscopic image.

Figure 3:
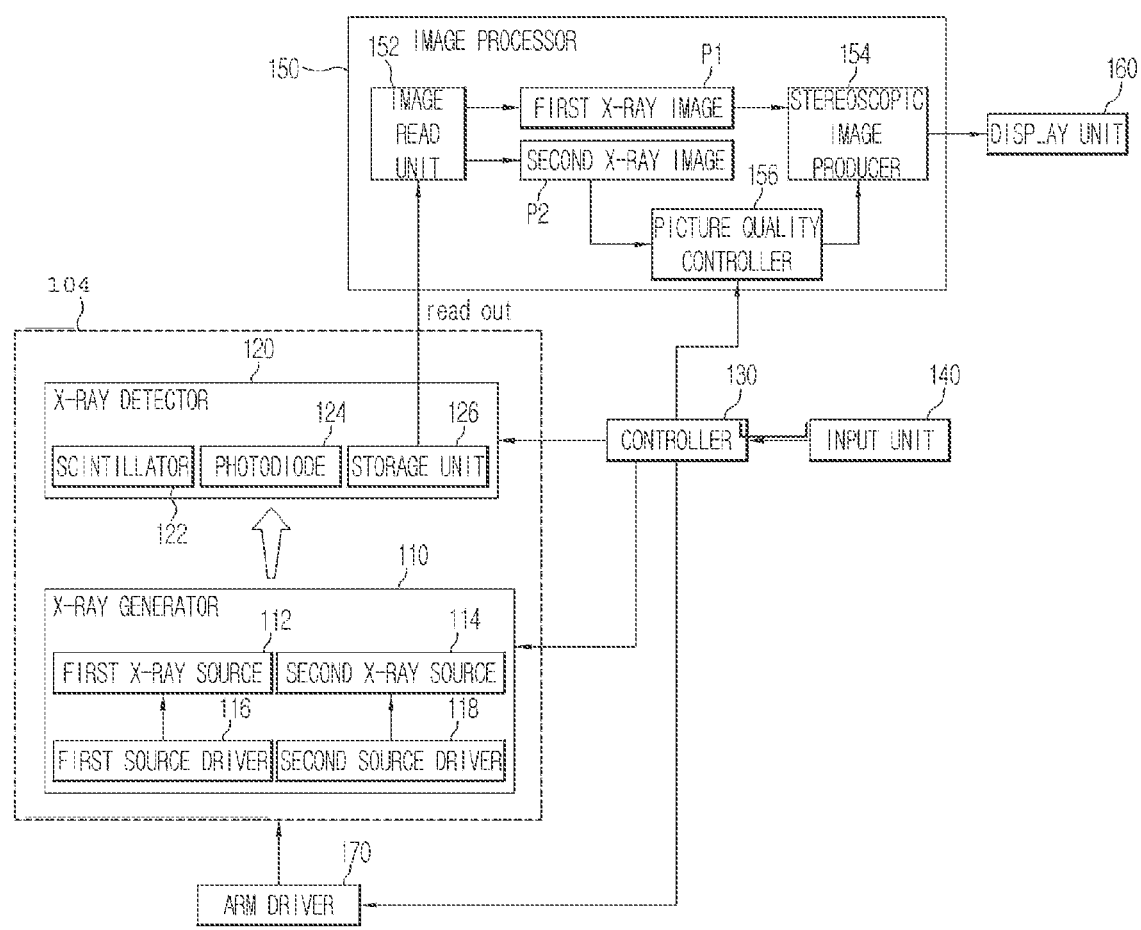
FIG. 3 is a control block diagram of an X-ray imaging apparatus.

FIG. 3 is a control block diagram of an X-ray imaging apparatus.

Referring to FIG. 3, an X-ray imaging apparatus 100 may include an X-ray generator 110 configured to generate X-rays and to irradiate the X-rays onto an object ob, an X-ray detector 120 configured to receive the X-rays which are irradiated from the X-ray generator 110 and which then have propagated through the object ob, to convert the X-rays into electrical signals, and to store the electrical signals, an image processor 150 configured to read out an X-ray image from the X-rays converted into the electrical signals through the X-ray detector 120, and to perform image processing on the X-ray image, a display unit 160 configured to display the X-ray image read out or image-processed by the image processor 150 for a user, an arm driver 170 configured to rotate a C-arm 104 in which the X-ray generator 110 and the X-ray detector 120 are installed, and a controller 130 configured to control the X-ray generator 110, the X-ray detector 120, the image processor 150, the display unit 160, and the arm driver 170.

The X-ray generator 110 may include a first X-ray source 112 and a second X-ray source 114, and the first X-ray source 112 and the second X-ray source 114 may independently irradiate X-rays onto the object ob so as to photograph X-ray images of the object ob at a plurality of locations.

In detail, the first X-ray source 112 may irradiate a first X-ray onto the object ob so that the X-ray imaging apparatus 100 can acquire a first X-ray image of the object ob via the X-ray detector 120 and the image processor 150.

In addition, the second X-ray source 114 may irradiate a second X-ray onto the object ob at a different angle or location from that of the first X-ray source 112 so that the X-ray imaging apparatus 100 can acquire a second X-ray image of the object ob via the X-ray detector 120 and the image processor 150.

Accordingly, the X-ray imaging apparatus 100 may acquire a plurality of X-ray images of the object ob by using the plurality of X-ray sources 112 and 114.

Further, the X-ray generator 110 may include a first source driver 116 configured to translate the first X-ray source 112, and a second source driver 118 configured to translate the second X-ray source 114. The first and second source drivers 116 and 118 may include motors configured to generate power, and gears configured to transfer the generated power to the first and second X-ray sources 112 and 114, respectively.

The X-ray detector 120, which is a device configured for detecting X-rays which are irradiated by the X-ray generator 110 and which then have propagated through the object ob, may include a scintillator 122, a photodiode 124, and a storage unit (also referred to herein as a "storage device" and/or as a "storage") 126. The components and operations of the X-ray detector 120 will be described below in detail with reference to FIG. 6.

The controller 130 may be configured to control overall operations of the X-ray imaging apparatus 100. In detail, the controller 130 may generate control signals for controlling the individual components of the X-ray imaging apparatus 100, for example, the X-ray generator 110, the X-ray detector 120, the image processor 150, the display unit 160, and the arm driver 170, as illustrated in FIG. 3, and thus control the individual components of the X-ray imaging apparatus 100 by using the control signals. Specifically, the controller 130 may send control signals to the first and second X-ray sources 112 and 114 such that the first and second X-ray sources 112 and 114 irradiate an X-ray onto the object ob alternately. In addition, the controller 130 may send a control signal to the X-ray detector 120 such that the X-ray detector 120 alternately detects a first X-ray irradiated from the first X-ray source 112 in response to a switching pulse signal for switching to the first X-ray source 112 and then propagated through the object ob, and a second X-ray irradiated from the second X-ray source 114 in response to a switching pulse signal for switching to the second X-ray source 114 and then propagated through the object ob.

Further, the controller 130 may be configured to generate control commands for controlling the individual components of the X-ray imaging apparatus 100 according to a predetermined setting or according to an instruction or command input by a user via a separate input unit (also referred to herein as an "input device") 140, and to control the X-ray imaging apparatus 100 according to the control commands which are received from the input unit 140.

For example, the controller 130 may control the first X-ray source 112 and/or the second X-ray source 114 to translate the first X-ray source 112 and/or the second X-ray source 114, based on a translation command for translating the first X-ray source 112 and/or the second X-ray source 114, which is received via the input unit 140. Thereby, a distance (that is, a baseline distance d) between the first X-ray source 112 and the second X-ray source 114 is adjusted so as to adjust a cubic effect (depth) of a stereoscopic image that is produced by the X-ray imaging apparatus 100.

In addition, the controller 130 may control the C-arm 104 (see FIG. 1) to rotate, based on a rotation command for rotating the C-arm 104, which is received via the input unit 140. Thereby, the C-arm 104, including the X-ray generator 110 and the X-ray detector 120 that face each other, is rotated in order to change a viewpoint or a viewing angle.

The input unit 140 may enable the user to input commands for operations of the X-ray imaging apparatus 100, and the user may input any one or more of a radiography start command, a mode selection command for selecting a fluoroscopy mode, a Digital Subtraction Angiography (DSA) mode, a roadmapping mode, etc., a translation command for translating the first X-ray source 112 and/or the second X-ray source 114, and a rotation command for rotating the C-arm 104, via the input unit 140. Herein, the input unit 140 may include any one or more of various kinds of units or devices, such as a keyboard, a mouse, a trackball, a tablet, or a touch screen module, through which the user can input data, instructions, and/or commands.

The image processor 150 may produce an X-ray image of the object ob based on X-rays which have propagated through the object ob, and which are detected by the X-ray detector 120. Further, the image processor 150 may perform calibration for improving the picture quality of the X-ray image, including flat field correction and noise reduction, and the X-ray image of the object ob, subject to calibration, may be displayed via the display unit 160.

The image processor 150 may include an image read unit (also referred to herein as an "image reader device" and/or an "image reader") 152, a stereoscopic image producer 154, and a picture quality controller 156. Components and operations of the image processor 150 will be described in detail below with reference to FIG. 7.

The display unit 160 may display X-ray images acquired by radiography, and menus or guidance required for X-ray diagnosis. The display unit 160 may be embodied, for example, as a Cathode Ray Tube (CRT) or a Liquid Crystal Display (LCD).

The arm driver 170 may rotate the C-arm 104 in which the X-ray generator 110 and the X-ray detector 120 are installed, based on a control signal which is received from the controller 130.

Figure 4:
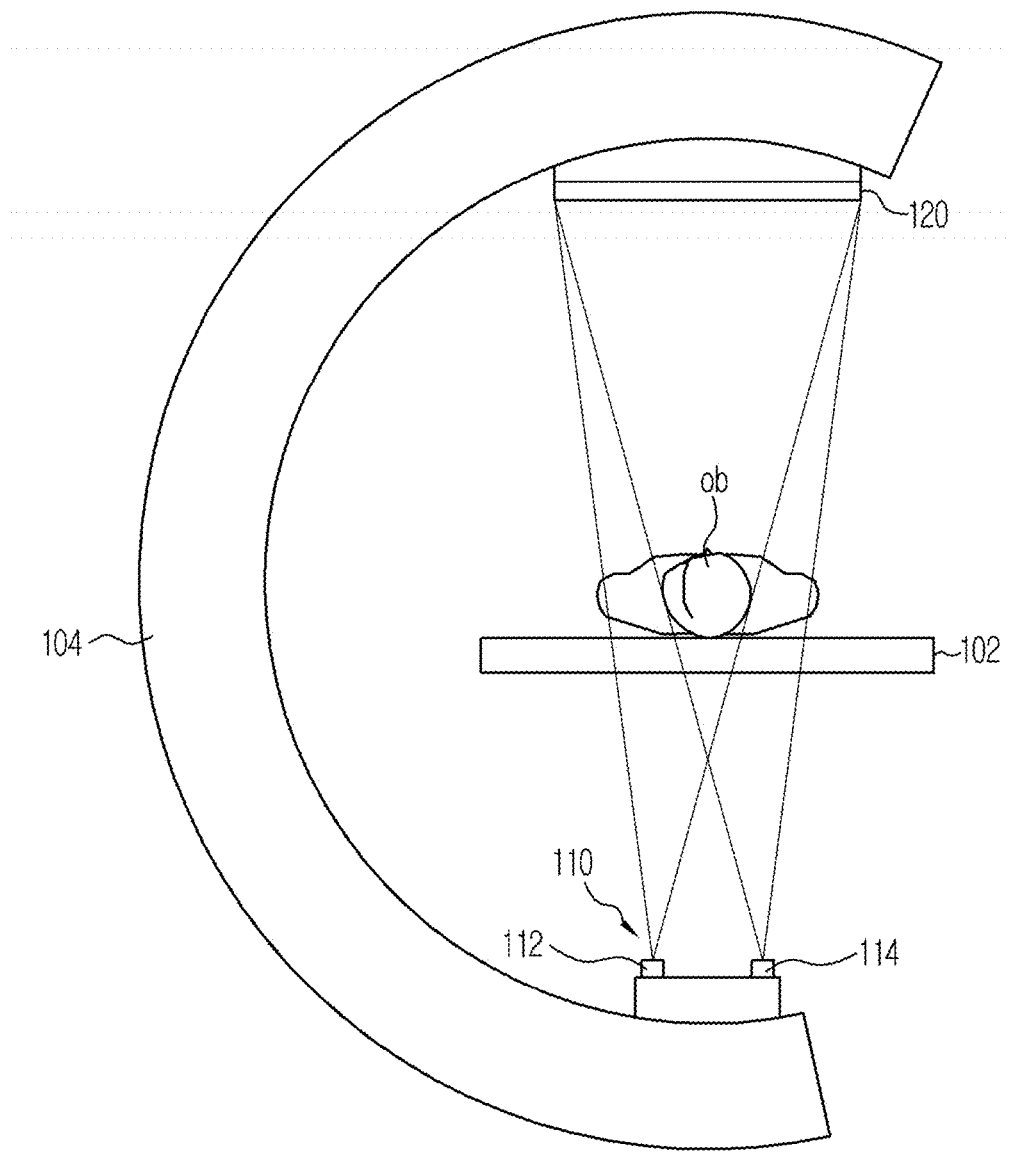
FIG. 4 illustrates an X-ray imaging apparatus (a symmetrical dual source system) which includes two X-ray sources arranged symmetrically.

FIG. 4 illustrates an X-ray imaging apparatus 100 (a symmetrical dual source system) which includes two X-ray sources 112 and 114 arranged symmetrically.

As illustrated in FIG. 4, an X-ray generator 110 may include two X-ray sources 112 and 114 (that is, a first X-ray source 112 and a second X-ray source 114) which are spaced by a predetermined distance apart from a central axis of a casing which constitutes the external appearance of the X-ray generator 110. Since the X-ray imaging apparatus 100 illustrated in FIG. 4 has a structure in which two X-ray sources 112 and 114 are arranged symmetrically with respect to the central axis of a casing, the X-ray imaging apparatus 100 is referred to as a symmetrical dual source system.

In order to enable the first X-ray source 112 and the second X-ray source 114 to alternately irradiate an X-ray toward an object ob during radiography, the controller 130 may generate a pulse signal for switching between the first X-ray source 112 and the second X-ray source 114. At this time, in order to produce a stereoscopic image for angiography in real time, a switching-on time of the pulse signal for switching between the first X-ay source 112 and the second X-ray source 114 must range from several milliseconds to tens of milliseconds. The switching-on time may have been stored in the controller 130 or a memory unit (not shown), or may be adjusted by a user.

The X-ray detector 120 may alternately detect a first X-ray irradiated from the first X-ray source 112 in response to a switching pulse signal for switching to the first X-ray source 112 and then propagated through the object ob, and a second X-ray irradiated from the second X-ray source 114 in response to a switching pulse signal for switching to the second X-ray source 114 and then propagated through the object ob, based on a switching pulse signal received from the controller 130. A first X-ray image P1 (e.g., a left image) produced based on the detected first X-ray and a second X-ray image P2 (e.g., a right image) produced based on the detected second X-ray may be displayed as 2D X-ray images on two monitors (display units 160). Alternatively, the first and second X-ray images P1 and P2 may be combined to produce a stereoscopic image for the object ob, and the stereoscopic image may be displayed on the display unit 160.

FIG. 4 relates to an example in which the X-ray detector 120 includes two X-ray sources 112 and 114, however, the X-ray detector 120 may be configured to include three or more X-ray sources, that is, an array source. If the X-ray detector 120 includes an array source, a stereoscopic image for an object ob may be produced based on multi-view X-ray images.

Figure 5:
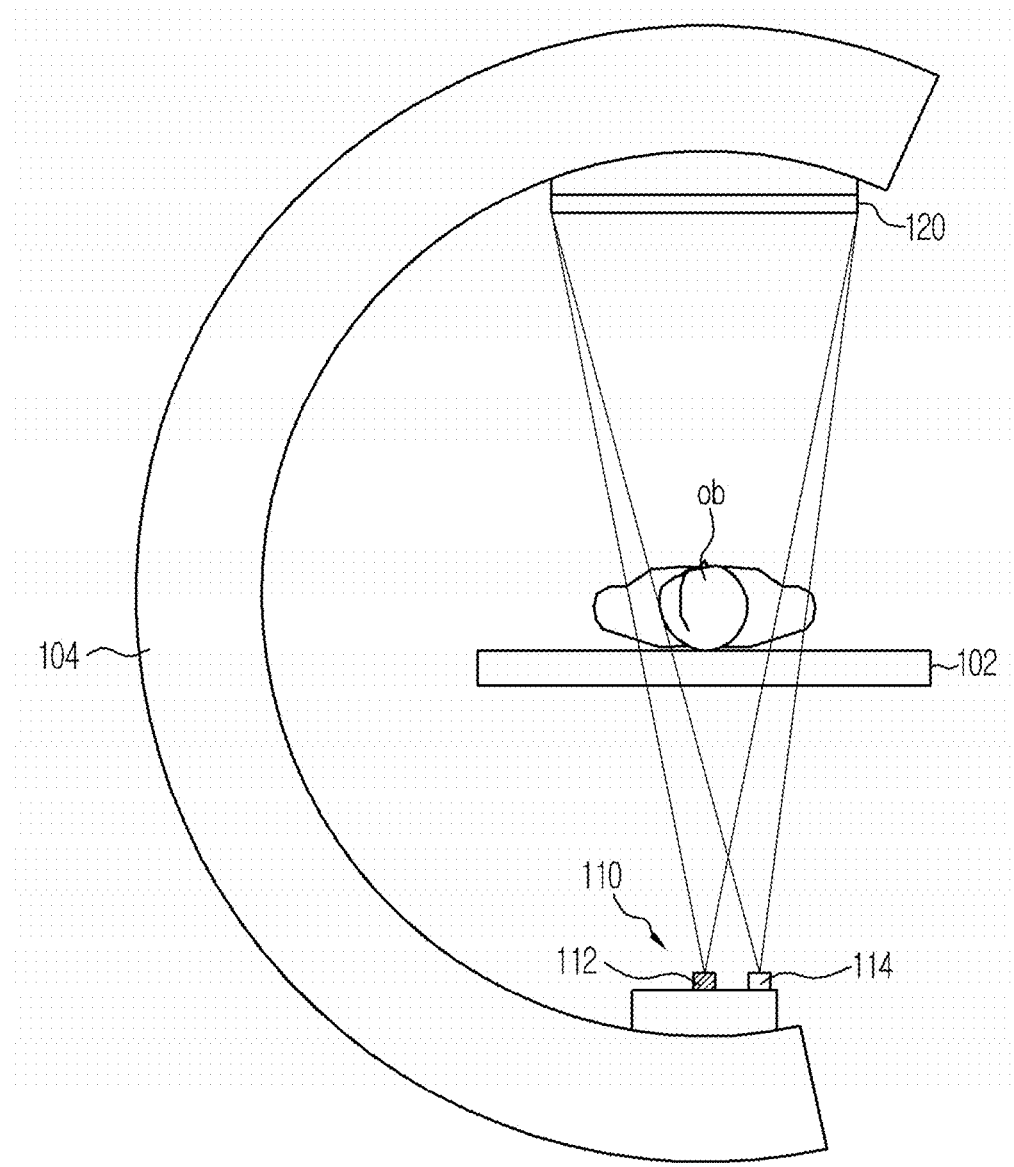
FIG. 5 illustrates an X-ray imaging apparatus (an asymmetrical dual source system) which includes two X-ray sources arranged asymmetrically.

FIG. 5 illustrates an X-ray imaging apparatus 100 (an asymmetrical dual source system) which includes two X-ray sources 112 and 114 arranged asymmetrically.

As illustrated in FIG. 5, an X-ray generator 110 may include a primary X-ray source 112 disposed on the central axis of a casing which constitutes an external appearance of the X-ray generator 110, and a secondary X-ray source 114 disposed at an edge of the casing. Since the X-ray imaging apparatus 100 illustrated in FIG. 5 has a structure in which the two X-ray sources 112 and 114 are arranged asymmetrically with respect to the central axis of the casing, the X-ray imaging apparatus 100 is referred to as an asymmetrical dual source system.

When an X-ray image of an object ob is acquired using one of the two X-ray sources 112 and 114 constituting the X-ray generator 110, generally, the primary X-ray source 112 denoted by oblique lines in FIG. 5 is used.

Further, when 3D depth information of complicated blood vessels is required in the DSA mode or the roadmapping mode, both the primary X-ray source 112 and the secondary X-ray source 114 may be used to acquire a stereoscopic image of an object ob. The asymmetrical dual source system has an advantage that the primary X-ray source 112 is located at an isocenter. When an X-ray image of an object ob is acquired using a single X-ray source, it is advantageous that the single X-ray source is located close to an isocenter. The secondary X-ray source 114 disposed at an edge of the casing is additionally used when 3D information about the inside of the object ob is needed.

Figure 6:
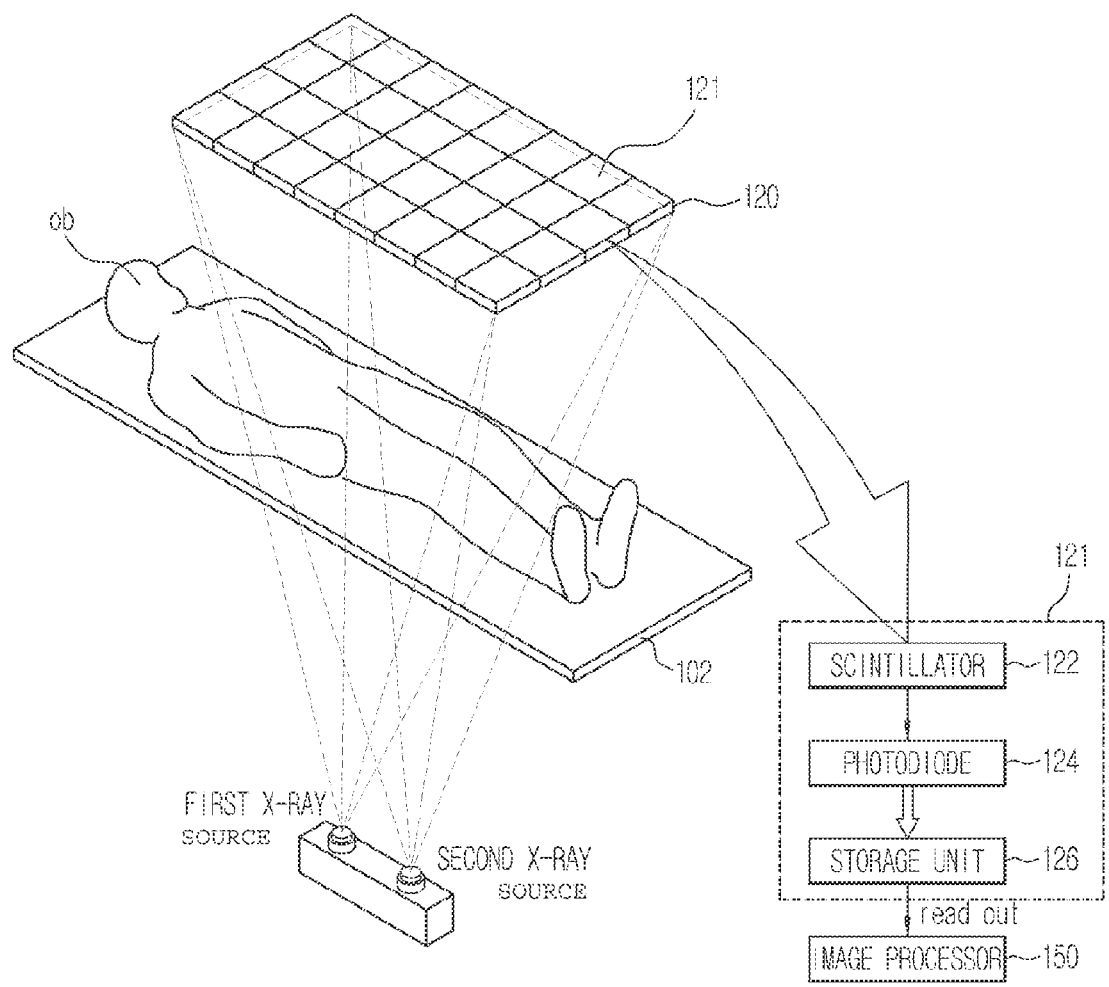
FIG. 6 is a view for describing an X-ray detection process that is performable by using an X-ray detector illustrated in FIG. 3.

FIG. 6 is a view for describing an X-ray detection process that is performed by the X-ray detector 120 illustrated in FIG. 3.

As illustrated in FIG. 6, the X-ray detector 120 may include a plurality of pixels 121 for receiving X-rays, and each pixel 121 may include a scintillator 122, a photodiode 124, and a storage unit (also referred to herein as a "storage device" and/or as a "storage") 126.

The scintillator 122 is made of a material of emitting light when receiving X-rays, and may receive X-rays irradiated from the X-ray generator 110 (see FIG. 3), that is, the first and second X-ray sources 112 and 114 (see FIG. 3) to emit photons. Then, the photodiode 124 may collect the photons, convert the collected photons into electrical signals, and store the electrical signals in the storage unit 126, for example, a storage capacitor, so that the X-ray detector 120 can detect X-rays. The electrical signals stored in the storage unit 126 and corresponding to the irradiated X-rays may be read out by the image processor 150, and the image processor 150 may produce an X-ray image corresponding to the irradiated X-rays based on the read-out electrical signals.

Hereinafter, a process in which a plurality of X-ray images photographed at different angles are produced, according to an exemplary embodiment, will be described.

Referring to FIG. 3, if the first X-ray source 112 irradiates a first X-ray toward an object ob and the X-ray detector 120, the X-ray detector 120 may convert the first X-ray which has propagated through the object ob into an electrical signal using the scintillator 122, the photodiode 124, and the storage unit 126, and store the electrical signal. The electrical signal may be read out by the image processor 150, specifically, the image read unit 152 of the image processor 150, and produced as a first X-ray image P1. After the first X-ray image P1 is produced, if the second X-ray source 114 irradiates a second X-ray toward the object ob and the X-ray detector 120, a second X-ray image P2 may be produced in the same manner. In particular, based on X-ray irradiations by the individual X-ray sources 112 and 114 of the X-ray generator 110, a plurality of X-ray images which correspond to X-ray irradiation locations of the respective X-ray sources 112 and 114 may be sequentially produced.

Figure 7:
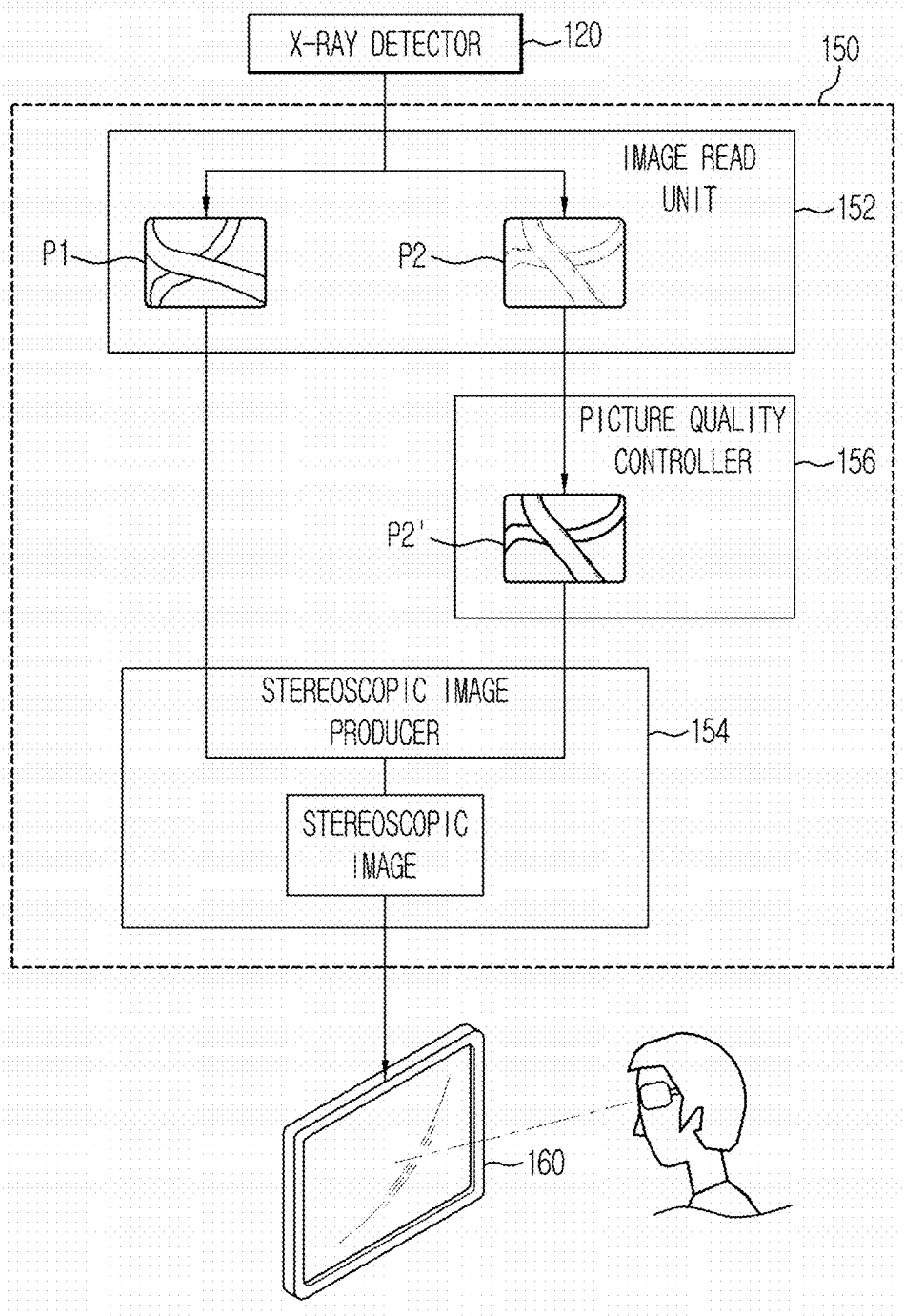
FIG. 7 is a view for describing an image processing process that is performable by using an image processor illustrated in FIG. 3.

FIG. 7 is a view for describing an image processing process (a stereoscopic image producing process) that is performable by using the image processor 150 illustrated in FIG. 3.

As illustrated in FIG. 7, the image processor 150 may include an image read unit (also referred to herein as an "image read device" and/or as an "image reader") 152, a stereoscopic image producer 154, and a picture quality controller 156.

The image read unit 152 may read out electrical signals stored in the storage unit 126 of the X-ray detector 120, and produce an X-ray image which corresponds to irradiated X-rays based on the electrical signals. Accordingly, a first X-ray image P1 and a second X-ray image P2 which respectively correspond to a first X-ray and a second X-ray may be produced via the image read unit 152, wherein the first and second X-ray images P1 and P2 are X-ray images of an object ob which are photographed at different angles due to a difference in locations of the first and second X-ray sources 112 and 114 (see FIG. 3).

The stereoscopic image producer 154 may produce a stereoscopic image using the read-out X-ray images, that is, the first and second X-ray images P1 and P2, or may control the display unit 160 to display the first and second X-ray images P1 and P2 according to a predetermined display method so that a user can see a stereoscopic X-ray image of the object ob.

The stereoscopic image producer 154 may perform image processing on the first and second X-ray images P1 and P2 such that a user can see 2D X-ray images three-dimensionally using binocular disparity, or the stereoscopic image producer 154 may control the display unit 160 to display the first and second X-ray images P1 and P2 three-dimensionally.

For example, the stereoscopic image producer 154 may perform predetermined image processing on the first and second X-ray images P1 and P2 in order to produce a stereoscopic image such that the first and second X-ray images P1 and P2 can be respectively used as an X-ray image for a left eye and an X-ray image for a right eye, or the stereoscopic image producer 154 may control the display unit 160 to display the first and second X-ray images P1 and P2 three-dimensionally.

When the stereoscopic image producer 154 performs the predetermined image processing on the first and second X-ray images P1 and P2 so that a user can see a stereoscopic X-ray image of the object ob, the stereoscopic image producer 154 may cause the baselines or centers of the first and second X-ray images P1 and P2 to be substantially identical to each other.

An example in which the stereoscopic image producer 154 produces a stereoscopic image is as follows. The stereoscopic image producer 154 may correct colors of each of the first and second X-ray images P1 and P2 by using a color filter. For example, the stereoscopic image producer 154 may correct the color of one of the first and second X-ray images P1 and P2 to a red color and the color of the other one of the first and second X-ray images P1 and P2 to a green color and then overlap the resultant first and second X-ray images P1 and P2 in order to produce a new combined image or to display the corrected first and second X-ray images P1 and P2 on a display unit 160.

Thereafter, if a user wears anaglyph glasses to see the first and second X-ray images P1 and P2 which are displayed on the display unit 160, the object ob corresponding to the first and second X-ray images P1 and P2 will be shown three-dimensionally.

Further, in order for a user to see a stereoscopic image using a passive polarized glasses method or a shutter glasses method, the stereoscopic image producer 154 may perform predetermined image processing on the first and second X-ray images P1 and P2. In addition, the stereoscopic image producer 154 may display the first and second X-ray images P1 and P2 subject to the predetermined image processing repeatedly on a display unit 160, so that a user can see a stereoscopic image by using polarized glasses and/or any other suitable device or mechanism.

Further, the two X-ray sources 112 and 114 may irradiate the same dosage of X-ray or different dosages of X-ray. For example, the first X-ray image P1 read out by the image read unit 152 may be an X-ray image acquired using a relatively higher dosage of a first X-ray than a second X-ray, and the second X-ray image P2 may be an X-ray image acquired using a relatively low dosage of the second X-ray than the first X-ray. In this case, the first and second X-ray images P1 and P2 may have different picture qualities due to the difference in dosage of first and second X-rays, and when a stereoscopic image is produced using two images having different picture qualities, the produced stereoscopic image may have a low cubic effect, or Visually Induced Motion Sickness (VIMS) may be caused. Accordingly, a process of causing the picture qualities of the first and second X-ray images P1 and P2 to be substantially identical to each other before producing a stereoscopic image is useful.

Accordingly, the image processor 150 may further include a picture quality controller 156 configured to improve a respective picture quality of X-ray images acquired using a relatively lower dosage of X-ray.

The picture quality controller 156 of the image processor 150 may improve a picture quality of the second X-ray image P2 acquired using a relatively lower dosage of X-ray before producing a stereoscopic image of the object ob, thereby causing the picture qualities of the first and second X-ray images P1 and P2' to be substantially identical to each other.

As such, if the picture qualities of the first and second X-ray images P1 and P2 are caused to be substantially identical to each other by the picture quality controller 156, when a stereoscopic image is produced and displayed using the first and second X-ray images P1 and P2, a degree of fatigue such as VIMS due to viewing stereoscopic images may be reduced.

FIG. 8 is a table showing examples of radiography protocols according to angiography modes, which are used upon radiography (angiography) using two X-ray sources.

Upon angiography, radiography modes may be largely classified into three modes: a fluoroscopy mode, a DSA mode, and a roadmapping mode. The fluoroscopy mode implements an imaging technique of using X-rays to acquire real-time moving X-ray images regarding the inside of an object ob using an X-ray fluoroscope. The fluoroscopy mode may be used to view only operation tools while monitoring a target area inside an object ob (for example, when there is no need to view blood vessels). The DSA mode implements a method of photographing X-ray images with a television camera before and after injecting a contrast medium, digitalizing the photographed X-ray images, and then performing subtraction on the digitalized X-ray images using two digital memory units to remove bones or soft tissue, thereby extracting only contrast blood vessel X-ray images. Accordingly, the DSA can acquire X-ray images with high contrast resolution using a small amount of a contrast medium, so as to obtain a clear arteries X-ray image by injecting an intravenous contrast medium. The roadmapping mode implements a technique of combining a blood vessel X-ray image acquired using X-rays with an image of operation tools, acquired using X-rays. The roadmapping is used when there is a need to distinguish the front and rear locations of operation tools, the front and rear locations of blood vessels, and the front and rear locations between operation tools and blood vessels.

Generally, during a cerebrovascular operation, a radiography mode may be changed as necessary. For example, a radiography mode may be changed in order of fluoroscopy mode->DSA mode->fluoroscopy mode->roadmapping mode->DSA mode->fluoroscopy mode, based on a request from a user (e.g., a doctor). Generally, in the fluoroscopy mode, only the first X-ray source 112 or the primary X-ray source 112 (see FIGS. 3, 4, and 5) may be used to monitor a target area and check operation tools. However, the second X-ray source 114 or the secondary X-ray source 114 (see FIGS. 3, 4, and 5) may be additionally used as necessary. Since the DSA mode or the roadmapping mode is used when there is a need to view complicated blood vessels of an object ob, three-dimensional (3D) depth information about the inside of the object ob will be used as useful information during an operation. In this case, both the first X-ray source 112 (or the primary X-ray source 112) and the second X-ray source 114 (or the secondary X-ray source 114) may be used.

As illustrated in FIG. 8, a protocol 1 is a protocol of turning on the first X-ray source 112 and turning off the second X-ray source 114 in all the angiography modes. When the protocol 1 is executed, in all the angiography modes, only the first X-ray source 112 is used to acquire X-ray images.

Further, a protocol 2 is a protocol of turning on both the first X-ray source 112 and the second X-ray source 114 in all the angiography modes. When the protocol 2 is executed, in all the angiography modes, both the first and second X-ray sources 112 and 114 are used to acquire X-ray images.

Still further, a protocol 3 is a protocol of turning on the first X-ray source 112 and turning off the second X-ray source 114 in the fluoroscopy mode, and turning on both the first and second X-ray sources 112 and 114 in the DSA mode and the roadmapping mode. In particular, the protocol 3 turns on only the first X-ray source 112 in the fluoroscopy mode for checking operation tools while monitoring a target area, and turns on both the first and second X-ray sources 112 and 114 in the DSA mode or the roadmapping mode that is used when there is a need to view complicated blood vessels of an object ob.

The table of FIG. 8 shows three radiography protocols, however, radiography protocols according to angiography modes may be modified in any one or more of various ways according to a user's requirements or according to a radiography environment.

Figure 9A:
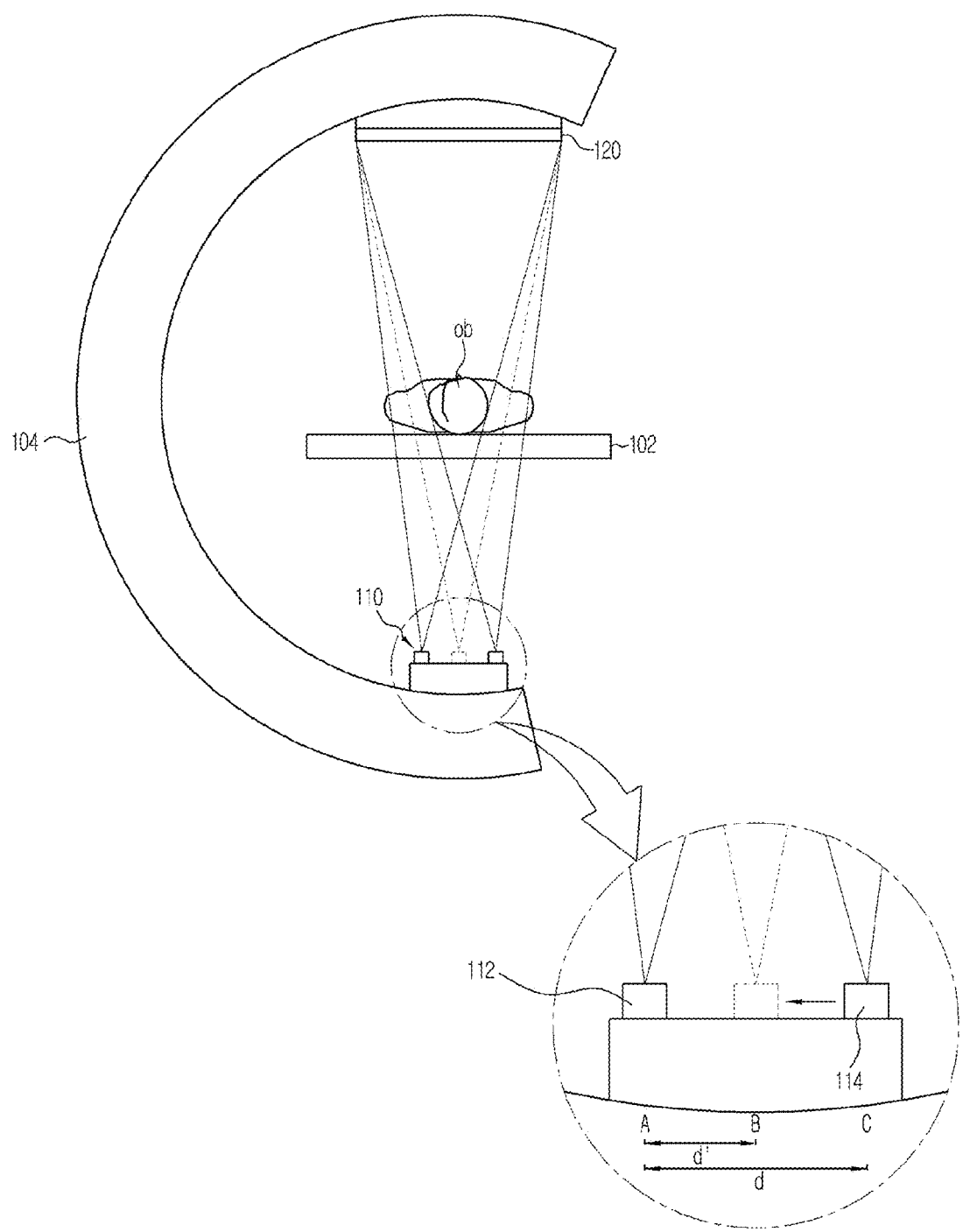
FIG. 9A illustrates an X-ray imaging apparatus which is capable of adjusting a distance (a baseline distance) between two X-ray sources arranged symmetrically.

FIG. 9A illustrates an X-ray imaging apparatus which is capable of adjusting a distance (a baseline distance) between two X-ray sources 112 and 114 arranged symmetrically.

Generally, if a distance (that is, a baseline distance) between two X-ray sources 112 and 114 increases, a cubic effect (depth) of a stereoscopic image is improved, and if the baseline distance between the two X-ray sources 112 and 114 decreases, the cubic effect of the stereoscopic image deteriorates. Accordingly, by adjusting the baseline distance between the two X-ray sources 112 and 114, a cubic effect of a stereoscopic image regarding the inside of the object ob can be adjusted. If the baseline distance between the X-ray sources 112 and 114 is longer than a second reference distance d2, a user may suffer from VIMS, although a cubic effect of a stereoscopic image is improved. In contrast, if the baseline distance between the X-ray sources 112 and 114 is shorter than a first reference distance d1, a cubic effect of a stereoscopic image may deteriorate, although a user is less likely to suffer from VIMS. Accordingly, the baseline distance between the X-ray sources 112 and 114 may be adjusted to a predetermined range (e.g., a range from between 5 cm and 10 cm) in which a user can experience a cubic effect of a stereoscopic image without suffering from VIMS, in consideration of a human's binocular disparity.

As illustrated in FIG. 9A, in a symmetrical dual source system in which the first X-ray source 112 is located at a point A, and the second X-ray source 114 is located at a point C, a baseline distance is a distance d between the point A and the point C. If the baseline distance d needs to be reduced in order to remove VIMS, the second X-ray source 114 may move in the direction of an arrow to approach the first X-ray source 112 until the second X-ray source 114 is located at a point B. Then, the baseline distance d is reduced to a distance d' between the point A and the point B. In FIG. 9A, an example of adjusting a distance between the two X-ray sources 112 and 114 by moving one (that is, the second X-ray source 114) of the two X-ray sources 112 and 114 is illustrated, however, in the symmetrical dual source system, either or both of the X-ray sources 112 and 114 may be moved to increase or decrease a baseline distance.

Figure 9B:
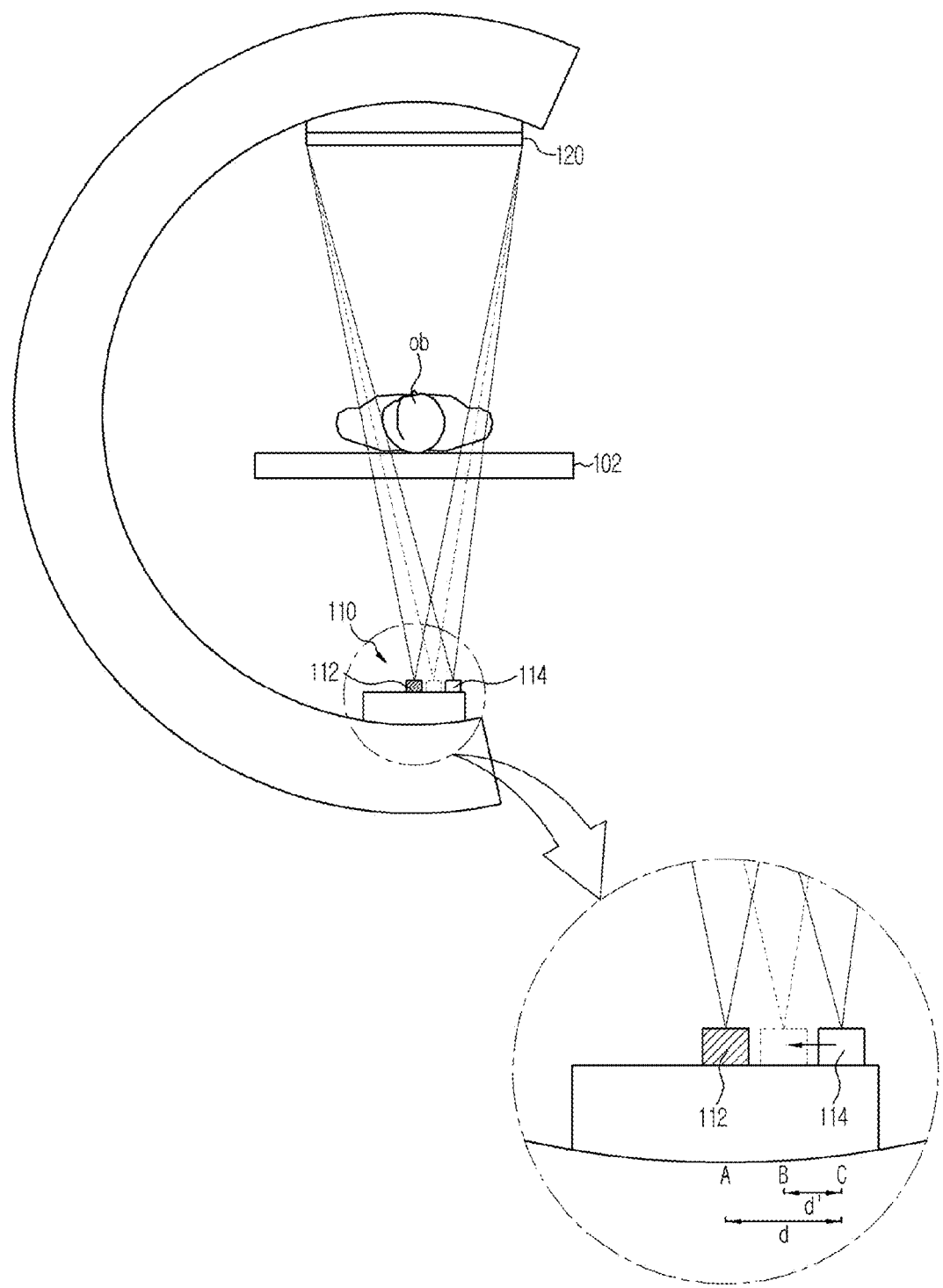
FIG. 9B illustrates an X-ray imaging apparatus which is capable of adjusting a distance between two X-ray sources arranged asymmetrically.

FIG. 9B illustrates an X-ray imaging apparatus 100 which is capable of adjusting a distance between two X-ray sources 112 and 114 arranged asymmetrically.

As illustrated in FIG. 9B, in an asymmetrical dual source system in which the primary X-ray source 112 is located at a point A, and the secondary X-ray source 114 is located at a point C, a baseline distance is a distance d between the point A and the point C. If the baseline distance d needs to be reduced in order to reduce a likelihood of VIMS, the secondary X-ray source 114 may move in the direction of an arrow to approach the primary X-ray source 112 until the secondary X-ray source 114 is located at a point B. Then, the baseline distance d is reduced to a distance d-d' between the point A and the point B. As such, in the asymmetrical dual source system, since the primary X-ray source 112 is always located at an isocenter, the baseline distance d is adjusted by moving the secondary X-ray source 114.

Figure 10:
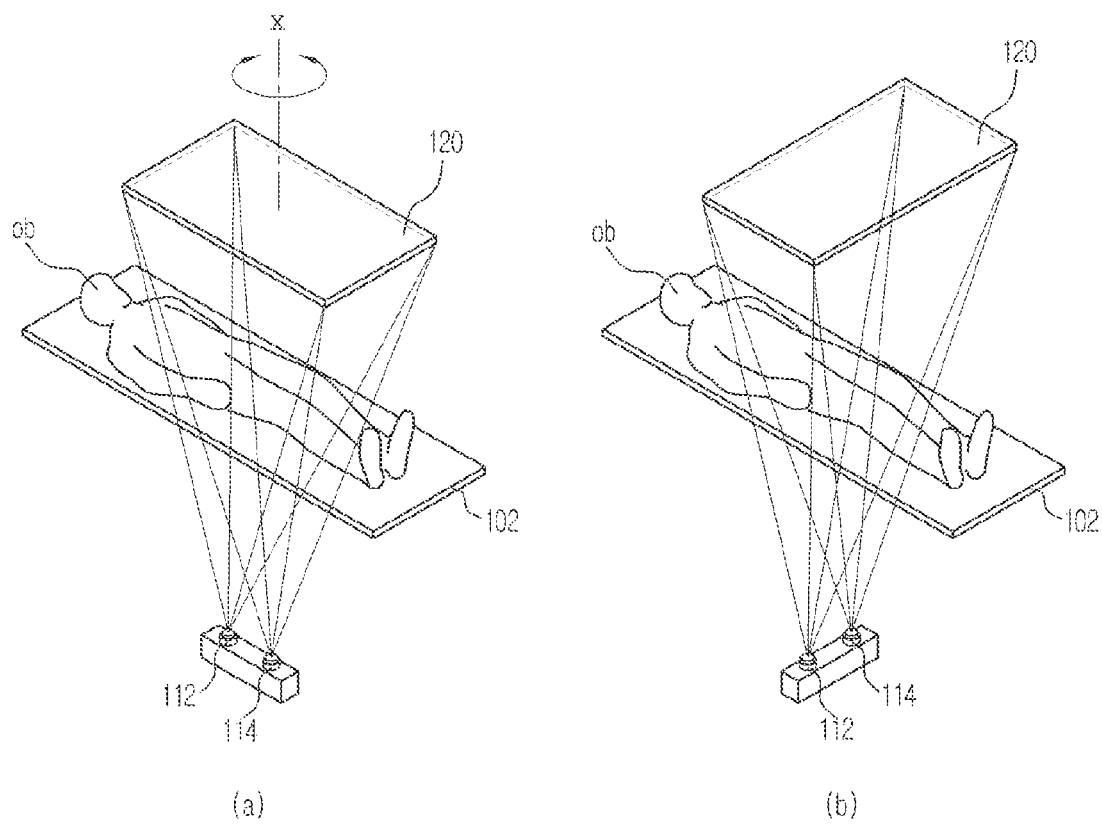
FIG. 10 illustrates an X-ray imaging apparatus in which two X-ray sources and an X-ray detector that face each other are rotatable.

FIG. 10 illustrates an X-ray imaging apparatus 100 in which two X-ray sources 112 and 114 and an X-ray detector 120 that face each other are rotatable.

When an object (e.g., a patient) ob is placed on a table 102, and the patient's inside is shown three-dimensionally, a radiography location or direction is very important. According to the structure of a patient's internal organs, which is to be examined or diagnosed, a better cubic effect may be obtained when the patient is observed from a viewpoint in the length direction of the object ob or when the patient is observed from a viewpoint in the width direction of the object ob. For example, according to the structure of a patient's internal organs, which is to be examined or diagnosed, the patient may be shown from a viewpoint in the length direction of the patient, as illustrated in drawing (a) as shown on the left side of FIG. 10, or from a viewpoint in the width direction of by rotating two X-ray sources 112 and 114 and an X-ray detector 120 by 90 degrees with respect to X-axis, as illustrated in drawing (b) as shown on the right side of FIG. 10.

Further, there may be a need to view the inside structure of an object ob in another direction than the length direction of the object ob or the width direction of the object ob. Accordingly, in order for a user to three-dimensionally view an inside structure of an object ob, a C-arm 104 (see FIG. 5) including the plurality of X-ray sources 112 and 114 and the X-ray detector 120 may be implemented to have a rotation degree of freedom, so that the user can have stereoscopic perception about an inside structure of an object ob in a desired direction.

Figure 11:
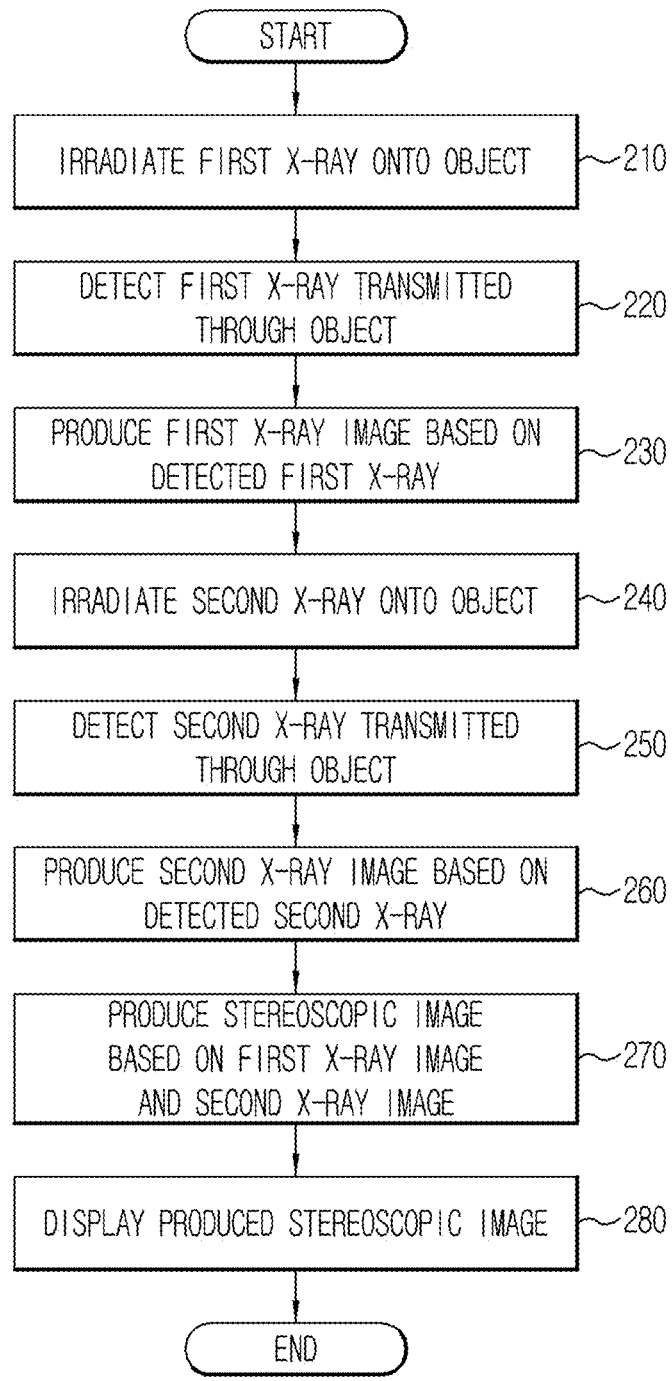
FIG. 11 is a flowchart of a control method which is executable by using an X-ray imaging apparatus.
Figure 12:
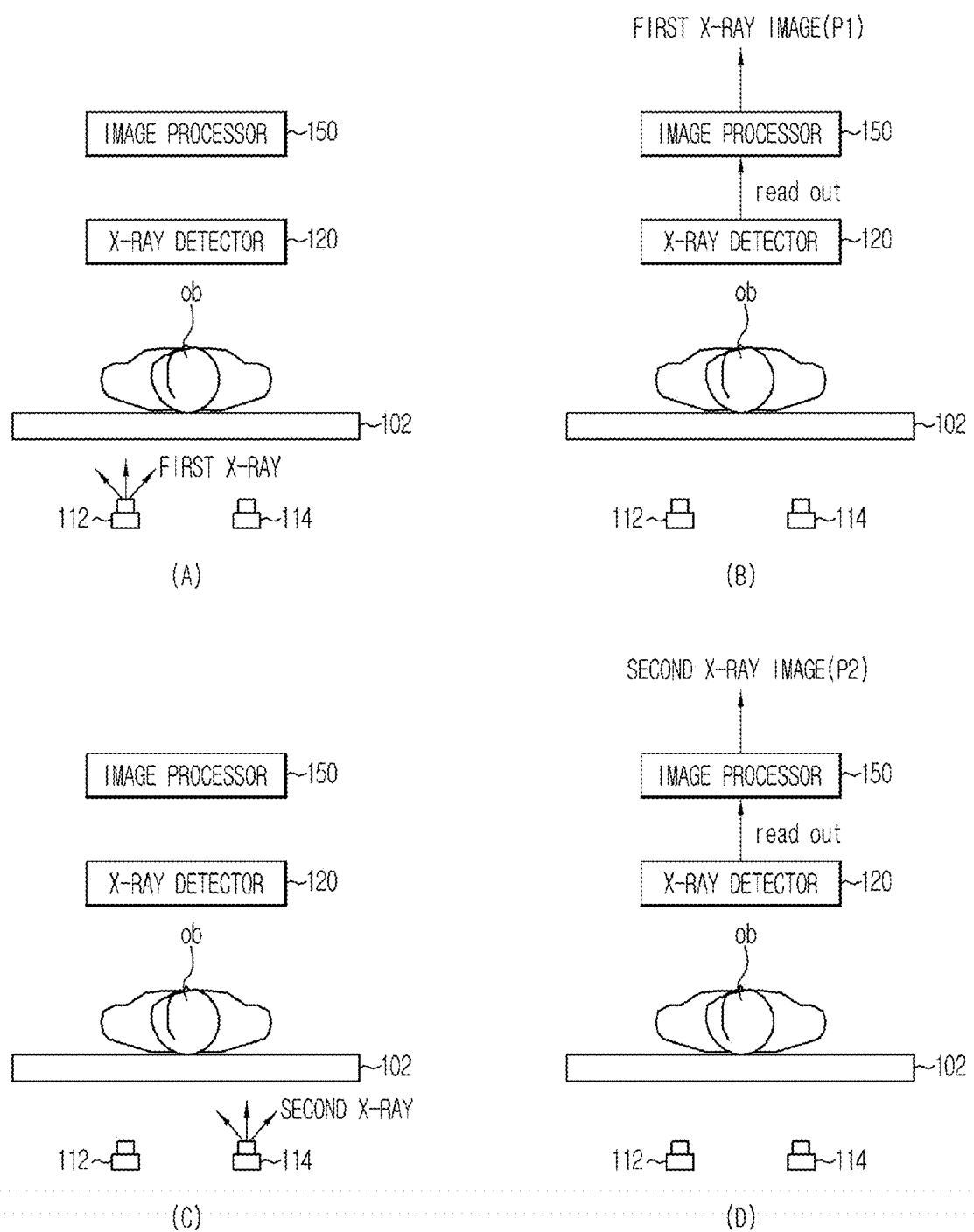
FIG. 12 is a view for describing a process of X-ray detection and X-ray image production using an X-ray imaging apparatus.

FIG. 11 is a flowchart of a control method which is executable by using an X-ray imaging apparatus 100, and FIG. 12 is a view for describing a process of X-ray detection and X-ray image production using an X-ray imaging apparatus 100.

In the exemplary embodiments illustrated in FIGS. 11 and 12, a process of acquiring two X-ray images of an object ob using two X-ray sources 112 and 114, and producing a stereoscopic image of the object ob based on the two acquired X-ray images is described.

Referring to FIGS. 3, 11, and 12, in operation 210, the first X-ray source 112 may irradiate a first X-ray toward the object ob, as illustrated in (A) of FIG. 12. Then, in operation 220, the X-ray detector 120 may detect the first X-ray which has propagated through the object ob using the scintillator 122, the photodiode 124, and the storage device 126, convert the first X-ray into an electrical signal, and store the electrical signal. Then, in operation 230, the image read unit 152 of the image processor 150 may read out the electrical signal from the storage unit 126, and convert the electrical signal into an X-ray image, thereby producing a first X-ray image P1 for the object ob from the first X-ray which has propagated through the object ob, as illustrated in (B) of FIG. 12.

Thereafter, in operation 240, the second X-ray source 114, which is spaced by a predetermined distance d apart from the first X-ray source 112, may irradiate a second X-ray toward the object ob, as illustrated in (C) of FIG. 12. In operation 250, the X-ray detector 120 may detect the second X-ray which has propagated through the object ob, and store the second X-ray in the storage unit 126. Then, in operation 260, the image read unit 152 of the image processor 150 may produce a second X-ray image P2 for the object ob from the second X-ray which has propagated through the object ob, as illustrated in (D) of FIG. 12).

In this way, the X-ray imaging apparatus 100 may acquire the first X-ray image P1 and the second X-ray image P2 of the object ob.

Thereafter, the picture quality controller 156 of the image processor 150 may perform image processing on at least one of the first and second X-ray images P1 and P2 of the object ob, thereby causing the picture qualities of the first and second X-ray images P1 and P2 to be substantially identical to each other.

Then, in operation 270, the stereoscopic image producer 154 of the image processor 150 may combine the first and second X-ray images P1 and P2 of the object ob in order to produce a new stereoscopic image (or a 3D image) of the object ob.

Thereafter, in operation 280, the controller 130 may send a control signal to the image processor 150 and the display unit 160 for the display unit 160 to display the stereoscopic image of the object ob.

According to the exemplary embodiments described above, the plurality of X-ray sources 112 and 114 may irradiate a plurality of X-rays toward an object ob, and the X-ray detector 120 may detect the plurality of X-rays which have propagated through the object ob, and produce a stereoscopic image of the object ob based on the detected X-rays. Accordingly, a user may three-dimensionally see at least one inner tissue of the object ob, for example, blood vessel tissue in the heart, so as to be able to quickly and accurately determine an existence or locations of lesions.

Although a few exemplary embodiments have been shown and described, it will be appreciated by those skilled in the art that changes may be made in these exemplary embodiments without departing from the principles and spirit of the present disclosure, the scope of which is defined in the claims and their equivalents.

What is claimed is:

1. An X-ray imaging apparatus comprising:
   an X-ray generator including a first X-ray source configured to irradiate a first X-ray onto an object, and a second X-ray source which is spaced apart from the first X-ray source and configured to irradiate a second X-ray onto the object;
   an X-ray detector configured to detect the first X-ray which has been transmitted through the object and the second X-ray which has been transmitted through the object;
   an image processor configured to produce a first X-ray image of the object based on the detected first X-ray, to produce a second X-ray image of the object based on the detected second X-ray, and to produce a stereoscopic image of the object based on the first X-ray image and the second X-ray image;
   an input device configured to receive, from a user, at least one from among a radiography mode selection command, a translation command for translating the first X-ray source and/or the second X-ray source, and a rotation command for rotating the X-ray generator and the X-ray detector; and
   a controller configured to control the X-ray generator and the X-ray detector based on a command which is received via the input device.

2. The X-ray imaging apparatus according to claim 1, wherein each of the first X-ray source and the second X-ray source is spaced by a predetermined distance apart from a central axis of the X-ray generator.

3. The X-ray imaging apparatus according to claim 1, wherein one of the first X-ray source and the second X-ray source is disposed on a central axis of the X-ray generator, and the other one of the first X-ray source and the second X-ray source is disposed at an edge of the X-ray generator.

4. The X-ray imaging apparatus according to claim 1, wherein the controller is further configured to adjust a baseline distance between the first X-ray source and the second X-ray source based on the translation command which is received via the input device.

5. The X-ray imaging apparatus according to claim 4, wherein the controller is further configured to adjust the baseline distance to within a range of between 5 centimeters and 10 centimeters.

6. The X-ray imaging apparatus according to claim 1, wherein the controller is further configured to drive at least one from among the first X-ray source and the second X-ray source based on the radiography mode selection command which is received via the input device.

7. The X-ray imaging apparatus according to claim 1, wherein the controller is further configured to rotate the X-ray generator and the X-ray detector based on the rotation command which is received via the input device.

8. The X-ray imaging apparatus according to claim 1, further comprising a display device configured to display the stereoscopic image of the object.

9. An X-ray imaging apparatus comprising:
an X-ray generator including a first X-ray source configured to irradiate a first X-ray onto an object, and a second X-ray source which is spaced apart from the first X-ray source and configured to irradiate a second X-ray onto the object;
an X-ray detector configured to detect the first X-ray which has been transmitted through the object and the second X-ray which has been transmitted through the object; and
an image processor configured to produce a first X-ray image of the object based on the detected first X-ray, to produce a second X-ray image of the object based on the detected second X-ray, and to produce a stereoscopic image of the object based on the first X-ray image and the second X-ray image,
wherein a dosage of the second X-ray is less than a dosage of the first X-ray.

10. The X-ray imaging apparatus according to claim 9, wherein the image processor is further configured to cause a picture quality of the first X-ray image to be substantially identical to a picture quality of the second X-ray image.

11. A control method which is executable by using an X-ray imaging apparatus, comprising:
irradiating a first X-ray onto an object;
detecting the first X-ray which has been transmitted through the object and using the detected first X-ray to produce a first X-ray image of the object;
irradiating a second X-ray onto the object at a location spaced by a predetermined distance apart from a location at which the first X-ray has been irradiated;
detecting the second X-ray which has been transmitted through the object and using the detected second X-ray to produce a second X-ray image of the object; and
producing a stereoscopic image of the object based on the first X-ray image and the at least one second X-ray image,
wherein a dosage of the second X-ray is less than a dosage of the first X-ray.

12. The control method according to claim 11, before producing the stereoscopic image of the object, further comprising causing a picture quality of the first X-ray image to be substantially identical to a picture quality of the second X-ray image.

13. The control method according to claim 11, further comprising displaying each of the first X-ray image and the second X-ray image on different respective screens.

14. The control method according to claim 11, further comprising displaying the stereoscopic image of the object.

15. The control method according to claim 11, further comprising receiving, from a user, a radiography mode selection command.

16. The control method according to claim 11, further comprising receiving, from a user, a translation command for translating at least one from among the first X-ray source and the second X-ray source.

17. The control method according to claim 11, further comprising receiving, from a user, a rotation command for rotating the X-ray generator and the X-ray detector.

* * * * *